United States Patent
Goh et al.

(10) Patent No.: US 7,495,117 B2
(45) Date of Patent: Feb. 24, 2009

(54) METAL CARBOXYLATE SALTS

(75) Inventors: Swee-Keng Goh, Singapore (SG); Jesuadimai Ignatius Xavier Antony, Singapore (SG); Hai-Meng Tan, Singapore (SG); Yeun-Mun Choo, Singapore (SG)

(73) Assignee: Kemin Industries, Inc., Des Moines, IA (US)

( * ) Notice: Subject to any disclaimer, the term of this patent is extended or adjusted under 35 U.S.C. 154(b) by 59 days.

(21) Appl. No.: 11/499,528

(22) Filed: Aug. 4, 2006

(65) Prior Publication Data

US 2008/0033196 A1 Feb. 7, 2008

(51) Int. Cl.
*C07F 13/00* (2006.01)
*C07F 11/00* (2006.01)
*C07F 7/00* (2006.01)
*C07F 1/00* (2006.01)

(52) U.S. Cl. .................. 556/49; 556/61; 556/105; 556/114; 556/147; 426/635; 426/648; 426/806

(58) Field of Classification Search ............ 556/49, 556/61, 105, 114, 147; 426/635, 648, 806
See application file for complete search history.

(56) References Cited

U.S. PATENT DOCUMENTS

| | | | |
|---|---|---|---|
| 2,135,031 A | 11/1938 | Brown | |
| 2,848,366 A | 8/1958 | Bertsch | |
| 2,904,573 A | 9/1959 | Oroshnik | |
| 2,985,559 A | 5/1961 | Leonard | |
| 3,091,626 A | 5/1963 | Carlosn | |
| 3,133,942 A * | 5/1964 | Hahl | 554/71 |
| 3,162,660 A * | 12/1964 | Crayton | 554/73 |
| 3,478,073 A | 11/1969 | Rydh | |
| 4,060,535 A * | 11/1977 | Cinco | 554/75 |
| 4,700,000 A | 10/1987 | Merkel | |
| RE32,909 E * | 4/1989 | Lionelle et al. | 556/131 |
| 5,591,878 A * | 1/1997 | Nelson et al. | 556/49 |
| 5,707,679 A * | 1/1998 | Nelson | 426/635 |
| 5,795,615 A * | 8/1998 | Nelson et al. | 426/648 |
| 6,670,494 B1 * | 12/2003 | Trusovs | 556/49 |
| 7,067,165 B2 * | 6/2006 | Hartle et al. | 426/74 |
| 7,220,426 B2 * | 5/2007 | Abdel-Monem et al. | 424/442 |

FOREIGN PATENT DOCUMENTS

| | | |
|---|---|---|
| GB | 1328494 | 8/1969 |
| RU | 2206506 | 6/2003 |

* cited by examiner

*Primary Examiner*—P. Nazario Gonzalez
(74) *Attorney, Agent, or Firm*—Kent A. Herink; Emily E. Harris

(57) ABSTRACT

A dietary source of mineral in the form of a metal carboxylate is prepared using the acid-base-like reaction. A salt of a carboxylate anion and a by-product cation is reacted in aqueous solution with a salt of a metal cation and a by-product anion under conditions which form a metal carboxylate and the by-product salt. Solutions formed in the reaction may be applied directly to a dry carrier to produce a dry dietary supplement or, alternatively, the solutions may be filtered to remove precipitated by-product salt and the filtrate used as a liquid dietary supplement. Preferably, a reducing agent, such as ascorbic acid, is added to help prevent the oxidation of divalent to trivalent form of a metal salt, when an easily oxidized divalent metal is used as starting material.

14 Claims, 2 Drawing Sheets

METAL CARBOXYLATE SALTS

BACKGROUND OF THE INVENTION

The invention relates generally to dietary sources of metals and carboxylates and, more specifically, to a method for the production of metal carboxyl ate and its use as a source of dietary supplement.

Dietary minerals, including iron, copper, manganese, magnesium, selenium, and zinc, are essential trace elements in human and animal nutrition and the deficiency of one or more of these minerals is a common nutritional problem. However, the absorption of many of these minerals in the biological system is significantly higher if offered from an organic source. Organic minerals in the form of metal carboxylates are proven to have superior bioavailability in the biological system.

Bertsch et al. and Martinez et al. (U.S. Pat. No. 2,848,366; British Patent 1,328,494) reported the preparation of ferrous fumigate, in which the preferred water-soluble numeric salt, sodium fumigate was reacted with the preferred water-soluble ferrous salt, ferrous soleplate at high temperature (70° C. to 94° C.), in a displacement reaction to produce ferrous fumigate.

Other prior arts approaches involving the preparation of iron carboxyl ate salts include classical acid-base reaction (U.S. Pat. No. 5,795,615; U.S. Pat. No. 5,591,878; U.S. Pat. No. 4,700,000), and oxidation reaction (U.S. Pat. No. 2,904,573).

In the reported prior art processes which utilize the classical acid-base neutralization reaction, the acid component, carboxylic acid, was reacted with the base component, a basic metal salt of carbonate, hydroxide, or oxide, to produce metal carboxyl ate.

In the reported prior art process which utilizes the oxidation reaction, powdered iron is heated with a nonferrous acid citrate to produce the desired ferrous citrate complex, accompanied with an increase in the oxidation state of iron from 0 to 2+, corresponding to an oxidation of iron to ferrous iron, respectively.

The present invention discloses a process for the preparation of metal carboxylates utilizing a different approach from those of the reported prior art. An acid-base-like reaction route is utilized in the preparation of metal carboxyl ate, in which the acid and base properties of the starting materials are different from those previously reported in prior arts, for example, U.S. Pat. Nos. 5,795,615, 5,591,878, and 4,700,000.

The basic component used in the present invention is an ammonium salt of carboxyl ate and the acid component is a metal salt having the property of a Lewis acid, and the reaction proceeds at controlled temperatures.

SUMMARY OF THE INVENTION

The present invention discloses an efficient and safe process for the preparation of metal carboxylates, which process proceeds at carefully controlled temperatures.

The intrinsic chemical characteristic and hence the function of the starting materials in the present disclosure uses a different approach from those of the prior art. In addition, the reaction conditions, such as the reaction temperature, have been carefully optimized to give preferred results.

The invention consists of the use of an acid-base-like reaction to make metal carboxylates. A basic ammonium salt of a carboxyl ate and a water-soluble metal salt of Lewis acid property are combined and allowed to react at room temperature initially, followed by reaction at a reduced temperature wherein the metal carboxyl ate is formed.

An excess molar ratio of carboxylic acid is added to ammonium hydroxide and the mixture is allowed to react, which results in the formation of the basic ammonium salt of the carboxyl ate. The water-soluble metal salt is added to the ammonium carboxyl ate base and the mixture is allowed to react at controlled temperatures, resulting in the formation of the metal carboxyl ate.

In the case of iron, a reducing agent may be added to the reaction mixture to prevent the rapid oxidation of ferrous, Fe(II) to ferric, Fe(III), when a water-soluble ferrous salt is used.

In a preferred embodiment, the basic ammonium salt of carboxyl ate is a water-soluble ammonium carboxyl ate salt and the water-soluble metal salt of Lewis acid property is a metal chloride.

DETAILED DESCRIPTION OF THE PREFERRED EMBODIMENTS

Figure 1:
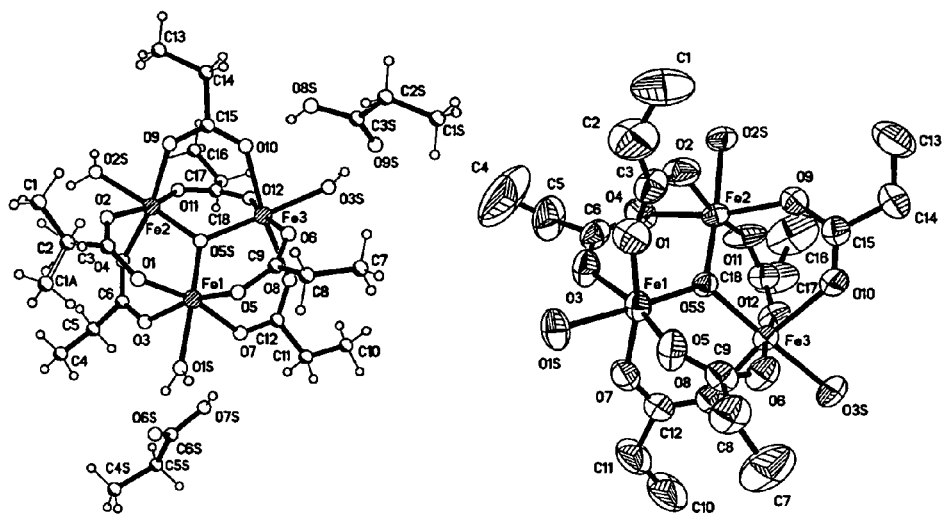
FIG. 1 is the X-ray diagram of iron propionate prepared from the present process.

The present invention relates to the preparation of metal carboxylates. The carboxyl ate component being the carboxyl ate moiety of the straight-chain monocarboxylic or polycarboxylic acid possessing 1 to 20 carbon atoms. The metal component is a water-soluble metal salt of Lewis acid property, with oxidation state of 2+ and 3+, corresponding to divalent and trivalent metal, respectively.

The proposed reaction mechanism between the ammonium carboxyl ate salt and divalent and trivalent metal salt are given below.

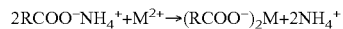

$$2RCOO^-NH_4^+ + M^{2+} \rightarrow (RCOO^-)_2M + 2NH_4^+$$

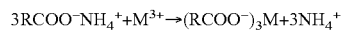

$$3RCOO^-NH_4^+ + M^{3+} \rightarrow (RCOO^-)_3M + 3NH_4^+$$

The approach taken in the present invention is different from those reported in prior art. For example, the carboxyl ate and metal components in the present invention are basic and acidic in property, respectively, contrary with those reported in the prior art. The carboxyl ate used in the present invention is the basic ammonium salt of straight-chain monocarboxylate or polycarboxylate possessing 1 to 20 carbon atoms. The metal used in the present invention is water-soluble divalent or trivalent metal salt of Lewis acid property.

The process involves reacting a carboxylic acid in excess molar ratio with ammonium hydroxide, resulting in the formation of the basic ammonium salt of the carboxyl ate. The water-soluble metal salt is added to the ammonium carboxyl ate base and the mixture is allowed to react at room temperature in the initial period, followed by reaction at a lower temperature in a chiller.

The temperature is carefully controlled through out the process in the present invention, in which at the reaction was carried out at room temperature (22-30° C.) in the initial period, followed by reaction at lower temperature (0-16° C.).

A reducing agent maybe also added in the reaction mixture to prevent the rapid oxidation of divalent metal ($M^{2+}$) to trivalent metal ($M^{3+}$), when an easily oxidized divalent metal is used, such as ferrous salt.

The products of the present invention have applicability as sources of metal in dietary supplements for humans and other animals. Accordingly, it is preferred that the starting materials, as well as the by-product are acceptable for consumption at the levels it is present in the completed reaction either before or after purification step.

The preferred embodiment of the present invention uses the ammonium salt of carboxyl ate as the basic carboxyl ate salt. The carboxylates component being the carboxyl ate moiety of the straight-chain monocarboxylic or polycarboxylic acid possessing 1 to 20 carbon atoms such as formic acid, acetic acid, prop ionic acid, 2-hydroxypropanoic acid, eicosapentaenoic acid, benzoic acid, 2-hydroxy-1,2,3-propanetricarboxylic acid, 1,2-ethanedicarboxylic acid, trans-1,2-ethenedicarboxylic acid, and hydroxybutanedioic acid.

While the metal chloride is the preferred water-soluble divalent or trivalent metal salt of Lewis acid property, other metal salts can be used, such as metal iodide, metal soleplate, and metal phosphate.

Additionally, the preferred water-soluble salt of Lewis acid property is divalent and trivalent, such as Fe(II), Fe(III), Mg(II), Cu(II), Zn(II), Cr(III), Co(II), Co(III), Mn(II), Mo(II), Mo(III), Ca(II), and Sn(II).

A reducing agent can be added to the reaction mixture to help prevent the oxidation of metal from oxidation state of 2+ to 3+, when divalent metal is used. While any compatible reducing agent could be used, such as many inorganic and organic compounds, food-grade organic compounds are preferred, including sodium metabisulfite and, in particular, ascorbic acid, in that ascorbic acid is believed to improve the bioavailability of iron in dietary supplements, one of the important applications of the products of the present invention.

The products of the present process may be administered as liquid dietary supplements, preferably by first passing the solution through a filter to remove any particulates. Alternatively, the products may be applied to a non-toxic silica, mineral, or clay based carriers, such as silica, vermiculite, betonies or gadolinite, to produce a dry dietary supplement. The product may or may not be filtered prior to application to the carrier.

EXAMPLE 1

Pure prop ionic acid and ammonium hydroxide solution (27%) in 1.3:1 molar ratio, respectively, were allowed to react at room temperature, which resulted in the formation of ammonium propionate, the basic component in the present invention. Ammonium propionate prepared from the previous step and a ferrous chloride solution (prepared from ferrous chloride solid and water), in a relative molar ratio of 2.1:1 were mixed together. To this mixture 10% w/w of 10% ascorbic acid solution was added and the reaction was allowed to proceed at room temperature in the initial period. The reaction was allowed to proceed at lower temperature (below 16° C.). Both the desired product and the by-product, which are iron propionate and ammonium chloride, respectively, precipitated out from the reaction solution.

EXAMPLE 2

Pure prop ionic acid and ammonium hydroxide solution (27%) in 1.3:1 molar ratio, respectively, were allowed to react at room temperature, which resulted in the formation of ammonium prop ionic, the basic component in the present invention. Ammonium propionate prepared from the previous step and ferrous chloride solution (prepared from ferrous chloride solid and water), in a relative molar ratio of 2.1:1 were mixed together. To this mixture 10% w/w of 10% sodium metabisulfite solution was added to prevent the oxidation of ferrous to ferric form. The reaction was allowed to proceed at room temperature in the initial period. The reaction was than proceed at lower temperature (below 16° C.). Both the desired product and the by-product, which are iron propionate and ammonium chloride, respectively precipitated out from the reaction solution.

EXAMPLE 3

Pure prop ionic acid and ammonium hydroxide solution (27%) in 1.3:1 molar ratio, respectively, were allowed to react at room temperature, which resulted in the formation of ammonium propionate, the basic component in the present invention. Ammonium propionate prepared from the previous step and magnesium chloride solution (prepared from magnesium chloride solid and water), in a relative molar ratio of 2.1:1 were mixed together and the reaction was allowed to proceed at room temperature in the initial period. The reaction was than proceed at lower temperature (between 0° C. and 16° C.). Both the desired product and the by-product, which are magnesium propionate and ammonium chloride, respectively, precipitated out from the reaction solution.

EXAMPLE 4

Pure prop ionic acid and ammonium hydroxide solution (27%) in 1.3:1 molar ratio, respectively, were allowed to react at room temperature, which resulted in the formation of ammonium propionate, the basic component in the present invention. Ammonium propionate prepared from the previous step and copper chloride solution (prepared from copper chloride solid and water), in a relative molar ratio of 2.1:1 were mixed together and the reaction was allowed to proceed at room temperature in the initial period. The reaction was than proceed at lower temperature (between 0° C. and 16° C.). Both the desired product and the by-product, which are copper propionate and ammonium chloride, respectively, precipitated out from the reaction solution.

EXAMPLE 5

Pure prop ionic acid and ammonium hydroxide solution (27%) in 1.3:1 molar ratio, respectively, were allowed to react at room temperature, which resulted in the formation of ammonium propionate, the basic component in the present invention. Ammonium propionate prepared from the previous step and manganese chloride solution (prepared from manganese chloride solid and water), in a relative molar ratio of 2.1:1 were mixed together and the reaction was allowed to proceed at room temperature in the initial period. The reaction was than allowed to proceed at lower temperature (between 0° C. and 16° C.). Both the desired product and the by-product, which are manganese propionate and ammonium chloride, respectively, precipitated out from the reaction solution.

EXAMPLE 6

Pure prop ionic acid and ammonium hydroxide solution (27%) in 1.3:1 molar ratio, respectively, were allowed to react at room temperature, which resulted in the formation of ammonium propionate, the basic component in the present invention. Ammonium propionate prepared from the previous step and zinc chloride solution (prepared from zinc chloride solid and water), in a relative molar ratio of 2.1:1 were mixed together and the reaction was allowed to proceed at room temperature in the initial period. The reaction was than allowed to proceed at lower temperature (between 0° C. and 16° C.). Both the desired product and the by-product, which are zinc propionate and ammonium chloride, respectively, precipitated out from the reaction solution.

EXAMPLE 7

Pure prop ionic acid and ammonium hydroxide solution (27%) in 1.3:1 molar ratio, respectively, were allowed to react at room temperature, which resulted in the formation of ammonium propionate, the basic component in the present invention. Ammonium propionate prepared from the previous step and cobalt chloride solution (prepared from cobalt chloride solid and water), in a relative molar ratio of 2.1:1 were mixed together and the reaction was allowed to proceed at room temperature in the initial period. The reaction was than proceed at lower temperature (between 0° C. and 16° C.). Both the desired product and the by-product, which are cobalt propionate and ammonium chloride, respectively, precipitated out from the reaction solution.

EXAMPLE 8

Pure prop ionic acid and ammonium hydroxide solution (27%) in 1.3:1 molar ratio, respectively, were allowed to react at room temperature, which resulted in the formation of ammonium propionate, the basic component in the present invention. Ammonium propionate prepared from the previous step and chromium chloride solution (prepared from chromium chloride solid and water), in a relative molar ratio of 2.1:1 were mixed together and the reaction was allowed to proceed at room temperature in the initial period. The reaction was allowed to proceed at lower temperature (between 0° C. and 16° C.). Both the desired product and the by-product, which are chromium propionate and ammonium chloride, respectively, precipitated out from the reaction solution.

EXAMPLE 9

Figure 2:
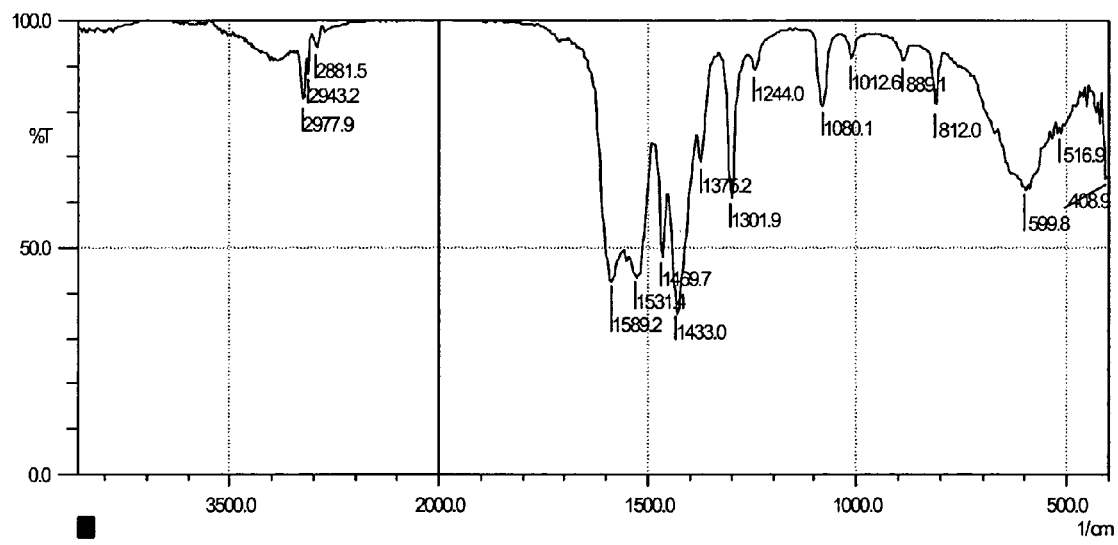
FIG. 2 is a chart of the Fourier transform infrared (FTIR) spectrum of iron propionate prepared from the present process.

The iron propionate from example 1 was crystallized from the reaction solution and was subjected to X-ray crystallography analysis. A total of 26704 reflections were collected by the $\phi$ and $\omega$ scans up to $\theta_{max}$ of 27.50° on a CCD area detector at 295 K using $MoK_\alpha$ ($\lambda$=0.717073 Å) radiation. The crystal dimensions are 0.54×0.32×0.24 mm. A total of 8810 reflections with $I>2\sigma(I)$ were observed. The structure was solved using SHELX-97 software. All non-hydrogen atoms were refined anisotropic ally by full matrix least squares refinement to R=0.0540, wR=0.1242 for the observed reflections, $w=[\sigma^2(F_o^2)+(0.0663P)^2+P^{-5}]^{-1}$, where $P=(F_o^2+2F_c^2)/3$. The crystal structure is given in FIG. 1. The Fourier Transform Infrared Spectroscopy (FTIR) spectrum of the iron propionate is given in FIG. 2.

The ammonium chloride from example 1 was crystallized from the reaction solution. The X-ray powder database confirmed the molecular integrity of the ammonium crystal.

Figure 3:
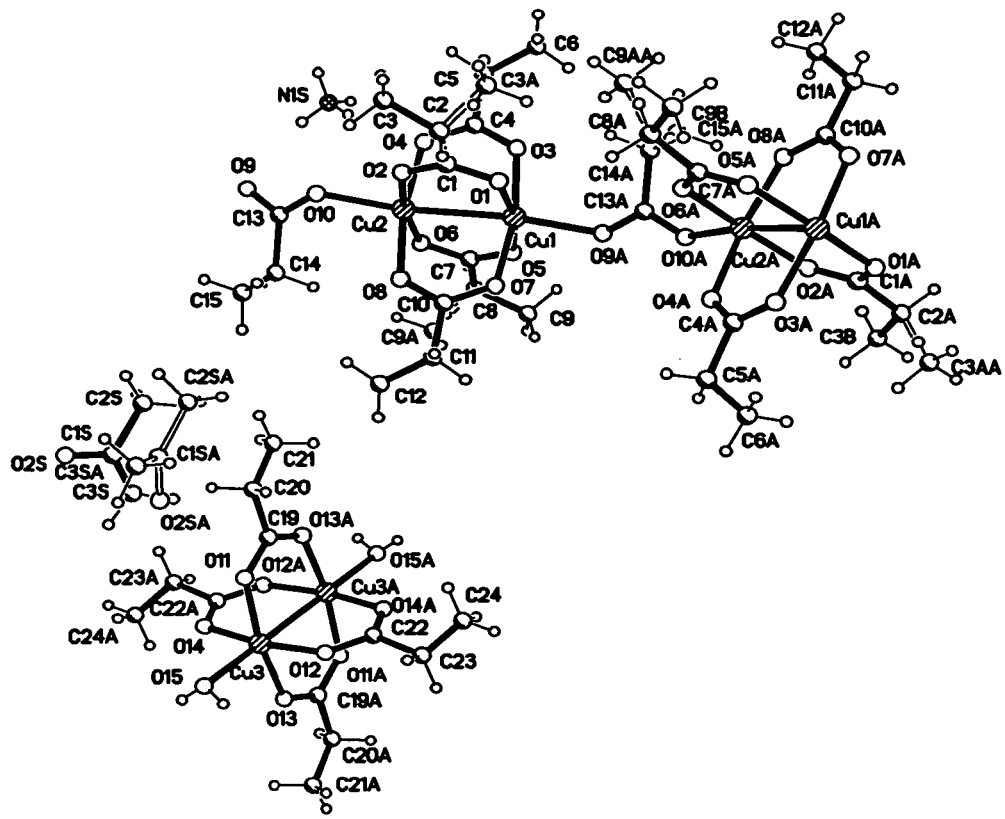
FIG. 3 is the X-ray diagram of copper propionate prepared from the present process.

The copper propionate from example 4 was crystallized from the reaction solution. Single crystal x-ray diffraction analysis gave the crystal structure of copper propionate as in FIG. 3.

Figure 4:
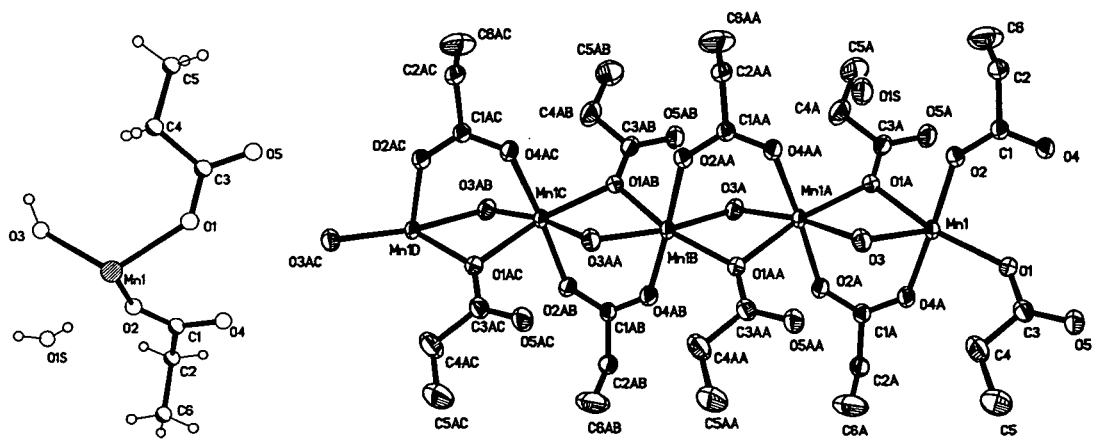
FIG. 4 is the X-ray diagram of manganese propionate prepared from the present process.

The manganese propionate from example 1 was crystallized from the reaction solution and the crystal structure is given in FIG. 4.

EXAMPLE 10

A variety of dry and liquid finished products can be made following the teachings of the present invention. The preferred embodiment of the process involves three primary steps: (i) Preparing the ammonium propionate by neutralization of prop ionic acid with ammonium hydroxide; (ii) preparing of the iron propionate by reacting the ammonium propionate and ferrous chloride in the presence of ascorbic acid in an optimized temperature system; and (iii) preparing the dry product by spraying the liquid product on a carrier.

In the first step 1.3 molar equivalent of prop ionic acid was admixed with 1 molar equivalent of ammonium hydroxide at room temperature. The resulting ammonium propionate was mixed with aqueous ferrous chloride solution in 2.1:1 molar ratio, respectively, and aqueous ascorbic acid solution. The reactants are allowed to react at room temperature in the initial period. The reaction was than allowed to proceed at lower temperature (between 0° C. and 16° C.). To make the liquid product, the reaction mixture may be filtered and the supernatant packaged or alternatively the reaction mixture is packaged directly. The dry product is made by mixing 1.9 parts of reaction mixture (liquid product without filtration), 1 part of carrier and 0.19 part of ascorbic acid. These ingredients are mixed in a ribbon blender until a uniform blend is achieved.

The present invention discloses a process to produce metal carboxylates. The process approach taken in the present invention is different from those reported in prior art in many aspects. The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:
1. A process for making a metal carboxylate using the acid-base-like reaction, comprising the steps of:
   (a) combining in a basic ammonium salt of a carboxylate and a water-soluble metal salt of Lewis acid property;
   (b) allowing the mixture to react at a temperature between 22 and 30° C. for a period of between 0 minutes and 15 minutes; and
   (c) reducing the temperature to between 0° C. and 16° C. for at least 15 minutes.

2. A process as defined in claim 1, wherein the carboxylate moiety is selected from the group consisting of the straight-chain monocarboxylic or polycarboxylic acid possessing 1 to 20 carbon atoms, and including formic acid, acetic acid, propionic acid, 2-hydroxypropanoicacid, eicosapentaenoic acid, benzoic acid, 2-hydroxy-1,2,3-propanetricarboxylic acid, 1,2-ethanedicarboxylic acid, trans-1,2-ethenedicarboxylic acid, and hydroxybutanedioic acid.

3. A process as defined in claim 1, wherein the water-soluble metal salt of Lewis acid property is selected from the group consisting of salts of Fe(II), Fe(III), Mg(II), Cu(II), Zn(II), Cr(III), Co(II), Co(III), Mn(II), Mo(II), Mo(III), Ca(II), and Sn(II).

4. A process as defined in claim 2, wherein the ammonium salt of carboxylate is formed by the reaction of the corresponding carboxylic acid and ammonium hydroxide.

5. A process as defined in claim 1, further comprising the addition of a reducing agent.

6. A process as defined in claim 5, wherein the reducing agent is an inorganic or organic compound.

7. A process as defined in claim 6, wherein the organic compound is a food-grade organic compound.

8. A process as defined in claim 7, wherein the food-grade organic compound is ascorbic acid.

9. A process for forming a metal carboxylate and a by-product salt using an acid-base-like reaction, comprising the step of combining in aqueous solution a water-soluble salt having a carboxylate anion and a by-product ammonium cation and a water-soluble salt having a metal cation and a by-product anion.

10. A process as defined in claim 9, further comprising the step of adjusting the temperature of the reaction from an initial high temperature to a low temperature so that products precipitate out of the solution.

11. A process as defined in claim 9, wherein the by-product anion is selected from the group consisting of chloride, iodide, sulphate, and phosphate.

12. A process as defined in claim 9, further comprising the step of adding a reducing agent to the solution.

13. A process as defined in claim 12, wherein the organic acid is a food-grade organic compound.

14. A process as defined in claim 13, wherein the food-grade organic compound is ascorbic acid.

* * * * *